United States Patent [19]

Zhukov et al.

[11] 4,101,600

[45] Jul. 18, 1978

[54] METHOD OF DIMERIZATION OF ALPHA-OLEFINS

[76] Inventors: Viktor Ivanovich Zhukov, ulitsa Neftezavodskaya, 4, kv. 1; Nikolai Petrovich Shestak, Pyatigorsky pereulok, 3, kv. 5, both of Grozny; Gennady Petrovich Belov, Noginsky raion, Chernogolovka, Shkolny bulvar, 5, kv. 53, Moskovskaya oblast; Maria Nikolaevna Dyadjunova, ulitsa Mozdokskaya, 1, kv. 2, Grozny; Leonid Alexandrovich Shilov, ulitsa Polezhaeva, 7, kv. 27, Grozny; Ivan Davydovich Shevlyakov, ulitsa Nakhimova, 162, kv. 19, Grozny; Fridrikh Stepanovich Dyachkovsky, Vorobievskoe shosse, $2^b$, kv. 9, Moscow; Alexandr Grigorievich Liakumovich, ulitsa Galeeva, 10, kv. 8, Kazan; Pavel Alexandrovich Vernov, Nizhnekamsk, ploschad 50 let Oktyabrya, 6, kv. 87, Tatarskaya ASSR; Jury Mikhailovich Sivakov, ulitsa Dybenko, 22, kv. 385, Moscow, all of U.S.S.R.

[21] Appl. No.: 769,426

[22] Filed: Feb. 17, 1977

[30] Foreign Application Priority Data

Feb. 23, 1976 [SU] U.S.S.R. .............................. 2320351

[51] Int. Cl.² ............................................. C07C 3/10
[52] U.S. Cl. ........................................ 260/683.15 D
[58] Field of Search ............................... 260/683.15 D

[56] References Cited

U.S. PATENT DOCUMENTS 3,564,071   2/1971   Izawa et al. ............... 260/683.15 D

*Primary Examiner*—C. Davis
*Attorney, Agent, or Firm*—Lackenbach, Lilling & Siegel

[57] ABSTRACT

The method of dimerization of alpha-olefins consists in mixing at least one alpha-olefin with a two-component catalyst consisting of organic compounds of titanium, having the general formula $Ti(OR)_4$, and of aluminum, having the general formula $AlR_3$, where R is an alkyl having from 1 to 6 carbon atoms, or an aryl, in a medium of a hydrocarbon solvent, at a temperature of 0° to 100° C and a pressure from 1 to 30 atm. Said constituents of the catalyst are pretreated with an ethylene-hydrogen mixture, containing from 5 to 95 percent by volume of hydrogen, at a temperature of from 0° to 100° C and a pressure of the ethylene-hydrogen mixture from 0.2 to 15 atm., for a period of time from 1 to 120 minutes. The method ensures high yields of butene-1 and hexenes, and high selectivity of the catalyst to said products. The butene-1 content of the butane mixture obtained in the process of ethylene dimerization is as high as 99 percent. The yield of butene-1 is from 80 to 345 g per gram of $Ti(OR)_4$ per hour. The hexene content in the dimerizate obtained in the process of dimerization of propylene, or a mixture of ethylene and butene-1, is 25 percent. The yield of hexenes is from 4 to 80 g per gram of $Ti(OR)_4$ per hour. The formation of polymers is significantly reduced.

3 Claims, No Drawings

METHOD OF DIMERIZATION OF ALPHA-OLEFINS

The invention relates to petrochemistry, and more particularly it relates to methods of dimerization of alpha olefins. Olefin monomers are a valuable starting material used in petrochemical and chemical industries.

Known in the prior art are methods for dimerization of alpha-olefins, consisting in mixing at least one alpha-olefin with a two-component catalyst consisting of 1. titanium alcoholate and organoaluminium compounds of the $AlR_3$ or $AlR_2H$ type, where R is an alkyl or aryl, or 2. aluminum alkyl and titanium alcoholate, $Ti(OR)_4$, or zirconium alcoholate, $Zr(OR)_4$; in a medium of a hydrocarbon solvent, at a temperature of 0° to 100° C and a pressure of alpha-olefins of 1 to 20 atm.

Said methods do not allow producing butene-1 by dimerizing ethylene with high yields and selectivity. For example the yield of butene-1 is 17–60 g per gram of $Ti(OR)_4$ per hour, the selectivity being 78 to 92 percent. Moreover, said methods do not allow producing hexenes (e.g. 3-methyl-1-pentene, 4-methyl-1-pentene 2-ethyl-1-butene) by dimerizing propylene, or a mixture of ethylene with butene-1, in high yields and selectivity. For example, the yield of hexenes is 6 – 13.5 g/g $Ti(OR)_4$ per hour, the selectivity being 10.5 percent. Said hexenes are of considerable importance if used in homopolymerization and copolymerization reactions with alpha-olefins and dienes.

An essential disadvantage of the known methods is the formation of polymers only as side products, which drastically complicates the process of dimerization of alpha-olefins (e.g., in dimerization of ethylene, the polymer content of the resulting dimerizate is only 0.6 to 5.6 percent).

In order to increase the yield of butene-1 and hexenes and to improve the selectivity of the catalyst with respect to said products, as well as to reduce the formation of polymers, various modifying additives have been proposed for the known catalysts: organophosphorus compounds, alcohols, etc. or the process of dimerization is carried out in the presence of hydrogen under its constant pressure in the system from 1 to 20 atm.

The presence of said modifying additives in the composition of the catalyst and the presence of hydrogen in the reaction zone leads only to a insignificant increase in the yield of butene-1 and additional formation of hexenes.

Thus, the known methods are characterized by comparatively low yields of butene-1 and hexenes per unit weight of the catalyst. For example, the yield of butene-1 does not exceed 10 g, and of hexenes, 0.3 g per gram of titanium alcoholate during five hours.

It is an object of the invention to provide a method of dimerization of alpha-olefins ensuring high yields of butene-1 and hexenes.

Another object of the invention is to provide a method of dimerization of alpha-olefins that would considerably decrease the formation of polymers.

In accordance with these and other objects, the invention resides in the provision of a method of dimerization of alpha-olefins by mixing at least one alpha-olefin with a two-component catalyst consisting of organic compounds of titanium, having the general formula $(Ti(OR)_4$, and of aluminum, having the general formula $AlR_3$, where R is an aryl having from 1 to 6 carbon atoms, or an aryl, in a medium of a hydrocarbon solvent, at a temperature of 0° to 100° C and a pressure of alpha-olefins of 1–30 atm., in which method, according to the invention, said component of the catalyst are pretreated with an ethylene-hydrogen mixture containing from 5 to 95 percent of hydrogen, at a temperature of 0° to 100° C and a pressure of the ethylene-hydrogen mixture of 0.2 to 15 atm., for 1 to 120 minutes.

The catalyst used in the herein-proposed method has high selectivity with respect to butene-1 and hexenes, this property being given to the catalyst due to its pretreatment. The herein-proposed method ensures high yields of said products. For example, in dimerization of ethylene, the yield of butene-1 is from 80 to 345 g/g $Ti(OR)_4$ per hour; the concentration of butene-1 in the resultant mixture is 99 percent. The yield of hexene, in dimerization of propylene or a mixture of ethylene with butene-1, is from 4 to 80 g/g $Ti(OR)_4$ per hour; the hexene content in the resulting dimerizate is 25 percent. The proposed method considerably decreases the polymer content of the resulting dimerizate (e.g. in dimerization of ethylene, the polymer content in the dimerizate is only 0.4 percent).

The catalyst components, $Ti(OR)_4$ and $AlR_3$, can be treated with the ethylene-hydrogen mixture either separately or simultaneously. In the latter case the mixture of the components, or actually the catalyst, is treated. Said treatment can be carried out either in the reactor where the dimerization process will further be effected, or in any other vessel. Said components of the catalyst are used as solutions in hydrocarbon solvents (concentration of solutions, 1 to 80 g/l). These solutions are either mixed for their combined treatment with the ethylene hydrogen mixture, or treated separately and then mixed. As has already been said, the ethylene-hydrogen treatment of the catalyst is effected at a temperature of 0° to 100° C, a pressure of the mixture of 0.2 to 15 atm., and concentration of hydrogen in said mixture of 5 to 95 percent by volume; the catalyst treatment time is 1 to 120 minutes.

The proposed method of dimerization can be realized in intermittent-action apparatus (with stirring) or continuous-action through flow tubular reactors.

Individual alpha-olefins, ethylene, propylene, butene-1 and other higher olefins, or mixtures thereof, can be used as starting alpha-olefins in the proposed method.

The hydrocarbon solvents can be aliphatic, aromatic, or acyclic hydrocarbons. e.g. heptane, benzene, toluene, cyclohexane, etc.

For a better understanding of the invention, the following examples of its practical embodiment are given by way of illustration.

EXAMPLE 1

A solution (20 ml) of 0.25 g of tetrabutoxytitanium in n-heptane and a solution (20 ml) of 0.38 of triethylaluminum in n-heptane are treated separately with an ethylene-hydrogen mixture containing 63 percent by volume of hydrogen at a temperature of 27° C and a pressure of said mixture of 2.5 atm., for 7 minutes. Said solutions are then introduced into a dimerization reactor having a capacity of 850 ml, 500 ml of n-heptane are added, and then ethylene is fed continually. The dimerization conditions are: temperature 57° C, ethylene pressure 2.5 atm., reaction time, 1 hour.

The resultant product (92.4 g) consists of 0.38 g of polymer, 20.3 g of hexenes, the rest being butene-1. The yield of butene-1 is 277 g per gram of $Ti(OR)_4$ per hour.

EXAMPLE 2

An ethylene-hydrogen mixture containing 63 percent by volume of hydrogen is fed into a 850-ml dimerization reactor to a pressure of 10 atm. Then 0.5 g of tetrabutoxytitanium and 0.76 g of triethylaluminum, in the form of n-heptane solutions are added (each solution in the quantity of 250 ml). The catalyst is kept at this pressure and a temperature of 25° C for 10 minutes. The temperature in the reactor is then raised to 57° C, and ethylene is delivered thereinto; at a pessure of ethylene of 2.5 atm. dimerization reaction is conducted for two hours.

The yield of the product is 126.5 g. It consists of 0.1 g of a polymer, 31.5 g of hexenes, the rest being butene-1. The yield of butene-1 is 84 g/g $Ti(OR)_4$ per hour.

EXAMPLE 3

The procedure for pretreatment of the catalyst components with the ethylene-hydrogen mixture and the conditions of ethylene dimerization are the same as in Example 2, except that the hydrogen content in the ethylene-hydrogen mixture is 20 percent by volume.

The yield of product is 131.2. It consists of 0.22 g of a polymer, 14.2 g of hexenes, the rest being butene-1. The yield of butene-1 is 118 g/g $Ti(OR)_4$ per hour.

The yield of product obtained under the same conditions but with the catalyst non-treated with the ethylene-hydrogen mixture, is 51 g. The product consists of 1.4 g of a polymer, 2.5 g of hexenes, the rest being butene-1. The yield of butene-1 is 46 g/g $Ti(OR)_4$ per hour.

EXAMPLE 4

The procedure for the pretreatment of the catalyst components with the ethylene-hydrogen mixture and the ethylene dimerization conditions is the same as in Example 1. except that the hydrogen content in the ethylene-hydrogen mixture is 20 percent by volume. The catalyst is treated for one minute at a temperature of 100° C.

The yield of product is 61.5 g. It consists of 0.11 g of a polymer, 6.1 g of hexenes, the rest being butene-1. The yield of butene-1 is 222 g/g $Ti(OR)_4$ per hour.

EXAMPLE 5

The procedure for the pretreatment of the catalyst components with the ethylene-hydrogen mixture and the ethylene dimerization conditions are the same as in Example 2, except that the hydrogen content in the ethylene-hydrogen mixture is 95 percent by volume, and the pretreatment of the catalyst components is effected at a temperature of 0° C for 120 minutes.

The yield of product is 150.5 g. It consists of 0.3 g of a polymer, 46 g of hexenes, the rest being butene-1. The yield of butene-1 is 105 g/g $Ti(OR)_4$ per hour.

EXAMPLE 6

The pretreatment of the catalyst components and the ethylene dimerization process, is the same as described in Example 2, except that the hydrogen content in the ethylene hydrogen mixture is 5 percent by volume, the catalyst components are treated at a temperature of 80° C for 5 minutes, and the pressure of the ethylene-hydrogen mixture is 0.2 atm.

The yield of product is 142.2 g. It consists of 0.4 g of a polymer, 29 g of hexenes, the rest being butene-1. The yield of butene-1 is 112.5 g/g $Ti(OR)_4$ per hour.

EXAMPLE 7

The procedure for the pretreatment of the catalyst components with the ethylene-hydrogen mixture and the conditions for ethylene dimerization is the same as in Example 2, except that the dimerization temperature is 80° C.

The yield of product is 98 g. It consists of 0.5 g of a polymer, 23 g hexenes, the rest being butene-1. The yield of butene-1 is 75.5 g/g $Ti(OR)_4$ per hour.

EXAMPLE 8

The procedure for the pretreatment of the catalyst components with the ethylene-hydrogen mixture and for dimerization of ethylene is the same as in Example 1, except that the hydrogen content in the ethylene-hydrogen mixture is 30 percent by volume and the pressure of the ethylene-hydrogen mixture is 15 atm.

The yield of product is 114 g. It consists of 0.13 g of a polymer, 27.3 g of hexenes, the rest being butene-1. The yield of butene-1 is 347 g/g $Ti(OR)_4$ per hour.

EXAMPLE 9

The procedure for the pretreatment of the catalyst components with the ethylene-hydrogen mixture and for dimerization is the same as in Example 1, except that ethylene is admitted into the reaction zone in a mixture with propylene, thier volume ratio being 1:2.

The yield of product is 47.3 g. It consists of 42.5 percent by weight of butene-1, 42 percent by weight of pentenes, and 15.5 percent by weight of hexenes, which is equivalent to the yields of 80 g, 89 g and 29 g/g $Ti(OR)_4$ per hour respectively.

EXAMPLE 10

The procedure for the pretreatment of the catalyst with the ethylene-hydrogen mixture and for the dimerization process is the same as in Example 1, except that the hydrogen content in the ethylene-hydrogen mixture is 30 percent by volume, the ethylene-hydrogen mixture pressure is 15 atm., and the ethylene to propylene ratio is 1:3 by volume.

The yield of product is 52.8 g. It consists of 38 percent by weight of butene-1, 47.5 percent by weight of pentenes, and 14.5 percent by weight of hexenes, which is equivalent to the yields of 80 g, 120 g, and 28.8 g/g $Ti(OR)_4$ per hour respectively.

EXAMPLE 11

The procedure for the pretreatment of the catalyst components with the ethylene-hydrogen mixture and for the dimerization process is the same as in Example 1, except that propylene is delivered into the reaction zone instead of ethylene.

The yield of product is 2 g. It consists of 0.8 g of 4-methylpentenes, 1 g of 2-methyl-1-pentene, the rest being hexene-1, hexene-2, and 3-methyl-1-pentene.

EXAMPLE 12

The procedure for the pretreatment of the catalyst components with the ethylene-hydrogen mixture and for the dimerization of ethylene is the same as in Example 2, except that tetrabenzyltitanium alcoholate $Ti(OCH_2C_6H_5)_4$ is used instead of tetrabutoxytitanium.

The yield of product is 69.3 g. It consists of 0.8 percent by weight of a polymer, 18 percent by weight of hexenes, the rest being butene-1. The yield of butene-1 is 56 g/g $Ti(OR)_4$ per hour.

EXAMPLE 13

The procedure for the pretreatment of the catalyst components with the ethylene-hydrogen mixture the starting concentrations of the catalyst components and the process of ethylene dimerization is the same as in Example 2, except that tetraphenyltitanium alcoholate Ti(O-C$_6$H$_5$)$_4$ is used instead of tetrabutoxytitanium.

The yield of product is 86.3 g. It consists of 0.6 percent by weight of a polymer, 17 percent by weight of hexenes, the rest being butene-1. The yield of butene-1 is 70.7 g/g Ti(OR)$_4$ per hour.

EXAMPLE 14

The procedure for the pretreatment of the catalyst components with the ethylene-hydrogen mixture and the starting concentrations of the catalyst components is the same as described in Example 2, except that tetraethoxy titanium is used instead of tetrabutoxytitanium, and trimethylaluminum is used instead of triethylaluminum.

The specifications of the process for dimerization of ethylene are as follows: temperature, 0° C; ethylene pressure, 1 atm.; dimerization time, 2 hours; solvent, benzene.

The yield of the product is 22.8 g. It consists of 0.05 g of a polymer, 5 g of hexenes, the rest being butene-1. The yield of butene is 17.8 g/g Ti(OR)$_4$ per hour.

EXAMPLE 15

The pretreatment of the catalyst components with the ethylene-hydrogen mixture and also the starting concentrations of the catalyst components are the same as in Example 1. L Tetraisopropoxytitanium is used instead of tetrabutoxytitanium, and trihexylaluminum is used instead of triethylaluminum. The pretreatment of the catalyst components with the ethylene-hydrogen mixture is carried out at a temperature of 40° C under a pressure of 1.5 atm., for 7 minutes.

The specifications of the dimerization process are: temperature, 100° C; ethylene pressure, 30 atm.; dimerization time, 1 hour; solvent, toluene.

The yield of product is 38.7 g. It cousists of 0.18 g of a polymer, 8 g of hexenes, the reset being butene-1. The yield of butene-1 is 76 g/g Ti(OR)$_4$ per hour.

EXAMPLE 16

The procedure for the pretreatment of the catalyst components with the ethylene-hydrogen mixture the starting concentrations of the catalyst components, and the process of ethylene dimerization are the same as in Example 1, except that tribenzylaluminum is used instead of triethylaluminum, the solvent is hexane, and the ethylene pressure in the dimerization process is 17 atm.

The yield of product is 48.8 g. It consists of 0.4 g of a polymer, 12 g of hexenes, the rest being butene-1. The yield of butene-1 is 91 g/g (TI(OR)$_4$ per hour.

We claim:

1. In a method for the dimerization of alpha-olefins, wherein at least one alpha-olefin is mixed with a two component catalyst consisting of organic compounds of titanium, having the general formula Ti(OR)$_4$, and of aluminum, having the general formula AlR$_3$, where R is an alkyl having from 1 to 6 carbon atoms, or an aryl, in a medium of a hydrocarbon solvent, at a temperature from 0° to 100° C, and a pressure of alpha-olefins from 1 to 30 atm., the improvement which comprises the pretreatment of said constituents with an ethylene-hydrogen mixture containing from 5 to 95 percent by volume of hydrogen, said pretreatment being effected at a temperature of about 0° to 100° C, and a pressure of the ethylene-hydrogen mixture of about 0.2 to 15 atm., for about 1 to 120 minutes.

2. The method of claim 1 wherein the catalyst components, Ti(OR)$_4$ and AlR$_3$ are separately pretreated with the ethylene-hydrogen mixture.

3. The method of claim 1 wherein the catalyst components, Ti(OR)$_4$ and AlR$_3$ are simultaneously pretreated with the ethylene-hydrogen mixture.

* * * * *